United States Patent [19]

Ozasa et al.

[11] 4,376,200

[45] Mar. 8, 1983

[54] HETEROCYCLIC THIOMETHYLATION OF THE 3-POSITION OF 7-AMINOCEPHALOSPORANIC ACIDS

[75] Inventors: Teruaki Ozasa, Urawa; Teruya Kashiwagi, Ageo, both of Japan

[73] Assignee: Yamanouchi Pharmaceutical Co. Ltd., Tokyo, Japan

[21] Appl. No.: 137,632

[22] Filed: Apr. 7, 1980

[30] Foreign Application Priority Data

Apr. 19, 1979 [JP] Japan ............................ 54-48211

[51] Int. Cl.³ ........................................ C07D 501/18
[52] U.S. Cl. ................................. 544/26; 544/21; 544/27

[58] Field of Search ............... 544/28, 21, 16, 26, 544/29, 27, 30

[56] References Cited

U.S. PATENT DOCUMENTS

| | | | |
|---|---|---|---|
| 3,641,021 | 2/1972 | Ryan | 544/27 |
| 4,014,874 | 3/1977 | Peter et al. | 544/27 |
| 4,144,391 | 3/1979 | Hatfield | 544/30 |
| 4,312,986 | 1/1982 | Saikawa et al. | 544/27 |

*Primary Examiner*—Nicholas S. Rizzo
*Attorney, Agent, or Firm*—Burgess, Ryan and Wayne

[57] ABSTRACT

An improved process for the displacement of the acetoxy group of a 7-aminocephalosporanic acid by a heterocyclic thiol in the presence of sulfuric acid.

8 Claims, No Drawings

HETEROCYCLIC THIOMETHYLATION OF THE 3-POSITION OF 7-AMINOCEPHALOSPORANIC ACIDS

BACKGROUND OF THE INVENTION

1. Field of the Invention

This invention relates to a novel process for the displacement of the acetoxy group of a 7-aminocephalosporanic acid and, more particularly, to a novel process of producing 7-amino-3-heterocyclic thiomethyl-$\Delta^3$-cephem-4-carboxylic acids.

2. Description of the Prior Art

It is known to convert the acetoxymethyl group at the 3-position of a cephalosporanic acid to a heterocyclic thiomethyl group by reacting with a thiol as disclosed in U.S. Pat. No. 3,278,531. The inventors of the above-described patent report in other literature (J. D. Cooker, et al.; "Journal of Chemical Society"; 5015–5031(1965)) that the reaction is preferably performed, in general, in an aqueous medium under a neutral or basic condition at room temperature or a slightly lower temperature and when the reaction is performed under an acid condition, lactone is by-product and greatly reduces the yield for the desired product.

It is also known to perform the reaction of a 7-aminocephalosporanic acid having a free amino group at the 7-position and a thiol in the presence of boron trifluoride or the ether complex thereof to improve the yield (70–90%) as described in German Offenlegungsschrift No. 2,804,896 but this process encounters a difficulty in the point of using boron trifluoride which is a gaseous toxicant and the ether complex thereof shows strong inflammability.

It is further known that since a 7-aminocephalosporanic acid having a free amino group at the 7-position is insoluble in an organic solvent, the reaction of the aminocephalosporanic acid is preformed after improving the solubility thereof in an organic solvent by introducing thereto an acyl groups as disclosed in U.S. Pat. No. 4,144,391.

Under such a technical level, it has been desired for producing intermediates for obtaining useful cephalosporin derivatives to introduce a heterocyclic thiomethyl group to the 3-position of a 7-aminocephalosporanic acid having a free amino group at the 7-position thereof by a manner suitable for industrial practice.

SUMMARY OF THE INVENTION

According to this invention, the acetoxymethyl group at the 3-position of a 7-aminocephalosporanic acid having a free amino group at the 7-position can be converted into a heterocyclic thiomethyl group under an acid condition which has not been employed in conventional techniques owing to the possibility of forming by-products and reducing the yield for products, and further, the desired product can be obtained at high yield without the formation of by-products.

The invention provides a process of producing a 7-amino-3-heterocyclic thiomethyl-$\Delta^3$-cephem-4-carboxylic acid shown by general formula I

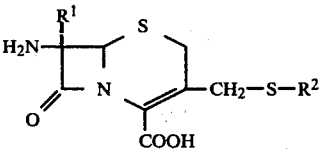

wherein $R^1$ represents a hydrogen atom or a methoxy group and $R^2$ represents a substituted or unsubstituted nitrogen-containing heterocyclic ring group or the salts thereof with a good yield and without the formation of by-products by reacting a 7-aminocephalosporanic acid shown by general formula II

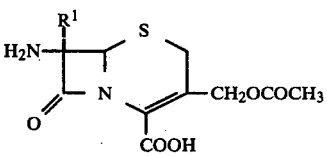

wherein $R^1$ has the same significance as in general formula I
or the salts thereof and a thiol shown by general formula III

HS—$R^2$      III wherein $R^2$ has the same significance as in general formula I in the presence of sulfuric acid.

DESCRIPTION OF THE PREFERRED EMBODIMENTS

Examples of the substituted or unsubstituted nitrogen-containing heterocyclic ring group shown by $R^2$ in the thiol (HS—$R^2$) used in this invention are, for example, a thiazolyl group, an oxazolyl group, an isothiazolyl group, a thiadiazolyl group, a triazolyl group, a tetrazolyl group, etc. these groups may have been substituted by a lower alkyl group such as a methyl group, ethyl group, isopropyl group, butyl group, etc.; a carboxyl lower alkyl group such as a carboxymethyl group, carboxyethyl group, carboxybutyl group, etc.; a di-lower alkylamino lower alkyl group such as a dimethylaminomethyl group, dimethylaminoethyl group, diethylaminomethyl group, diethylaminoethyl group, etc.; or an amino group.

Sulfuric acid used in this invention may be concentrated sulfuric acid or fuming sulfuric acid.

According to the practice of this invention, the compound of formula II is caused to react with an equimolar or excessive molar amount of the compound of formula III in the presence of sulfuric acid at room temperature or under heating. The amount of sulfuric acid used is usually more than 2 mole times, preferably more than 5 mole times the amount of the compound of formula II. In addition, at the reaction, sulfuric acid itself used acts as an inorganic solvent but, if necessary, polyphosphoric acid, etc., may be further used as an inorganic solvent.

The reaction is usually finished within several minutes to several hours. The desired product of formula I formed can be isolated from the reaction mixture by dispersing the reaction mixture in ice water and adjusting the pH of the solution to deposit the desired product. The product contains no by-products and hence the product can be induced into cephalosporin derivatives having excellent antibacterial activity as it is or without need of purification by introducing various acyl groups to the amino group at the 7-position thereof by a known method.

Some of the cephalosporin derivatives are illustrated below:

Cefamandole, Cefazolin, 7-(2-Aminothiazol-4-ylacetamido)-3-(1-β-dimethylaminoethyltetrazol-5-ylthiomethyl)-Δ³-cephem-4-carboxylic acid, 7β-Cyanomethylthioacetamido-7α-methoxy-3-(1-methyl-tetrazol-5-ylthiomethyl)-Δ³-cephem-4-carboxylic acid, 7β-(4-Carbamoyl carboxymethylene-1,3-dithietan-2-yl)carboxamido-7α-methoxy-3-(1-methyltetrazol-5-ylthiomethyl)-Δ³-cephem-4-carboxylic acid.

Then, the invention will further be explained by the following examples.

EXAMPLE 1

In 10 ml of concentrated sulfuric acid was dissolved 4.69 g of 5-mercapto-1-methyltetrazole and after adding thereto 10 g of 7-aminocephalosporanic acid, the obtained mixture was made to react for 54 minutes at a temperature of lower than 45° C. The reaction mixture formed was dissolved in 120 ml of ice water and the pH of the solution was adjusted to 3.7 under ice cooling. The precipitates thus deposited were recovered by filtration, washed successively with 40 ml of water and then 40 ml of acetone, and then dried to provide 9.65 g (yield 80%) of faint yellow 7-amino-3-(1-methyltetrazol-5-ylthiomethyl)-Δ³-cephem-4-carboxylic acid.

Melting point 205° C. (decomp.)

Nuclear magnetic resonance spectra (D₂O-DCl) ppm.

| 3.88 (2H, s, | $\underset{\text{H}}{\overset{\text{S}}{\diagup}}\!\!\!\diagdown\!\!\!\overset{\text{H}}{\diagdown}$ ), |
|---|---|
| 4.13 (3H, s, | $\diagup\!\!\!\text{N}-\text{CH}_3$), |
| 4.34 (2H, s, | $\underset{\text{CH}_2-\text{S}-}{\overset{\text{S}}{\diagup}}\!\!\!\diagdown$ ), |

5.20 (1H, J=5.8 Hz); 5.37 (1H, J=5.8 Hz)

Infrared absorption spectra: $\nu_{max}^{KBr}$: 1810 cm$^{-1}$ (β-lactam), 1620 cm$^{-1}$ (COO⁻)

EXAMPLE 2

In 6 ml of concentrated sulfuric acid was dissolved 1.41 g of 5-mercapto-1-methyltetrazole and after adding thereto 3.0 g of 7-aminocephalosporanic acid with stirring under ice cooling, the obtained mixture was made to react for 27 minutes. The reaction mixture obtained was dissolved in 70 ml of ice water and the pH of the solution was adjusted to 3.7 with aqueous ammonia under ice cooling. The precipitates thus formed were recovered by filtration, washed successively with 20 ml of water and then 20 ml of acetone, and dried to provide 3.22 g (89%) of faint yellow 7-amino-3-(1-methyltetrazol-5-ylthiomethyl)-Δ³-cephem-4-carboxylic acid. The values of the infrared absorption spectra, nuclear magnetic resonance spectra, and high pressure liquid chromatography of the product coincided with those of an authentic sample.

EXAMPLE 3

In 12 ml of concentrated sulfuric acid was dissolved 2.82 g of 5-mercapto-1-methyltetrazole and after adding thereto 6.0 g of 7-aminocephalosporanic acid with stirring under ice cooling, the obtained mixture was made to react for 28 minutes at 8°-14° C. The reaction mixture formed was dissolved in 140 ml of ice water and the pH of the solution was adjusted to 3.72 with aqueous ammonia under ice cooling. The precipitates thus formed were recovered by filtration, washed successively with 40 ml of water and then 40 ml of acetone, and dried to provide 6.91 g (90%) of 7-amino-3-(1-methyltetrazol-5-ylthiomethyl)-Δ³-cephem-4-carboxylic acid.

EXAMPLE 4

In a mixture of 6 ml of polyphosphoric acid (75%) and 6 ml of concentrated sulfuric acid was dissolved 1.41 g of 5-mercapto-1-methyltetrazole and after adding thereto 3.0 g of 7-aminocephalosporanic acid with stirring under ice cooling, the obtained mixture was made to react for 44 minutes at room temperature. The reaction mixture was dissolved in 70 ml of ice water and the pH of the solution was adjusted to 3.70 with aqueous ammonia under ice cooling. The precipitates formed were recovered by filtration, washed with 20 ml of water and 20 ml of acetone, and dried to provide 2.90 g (80%) of 7-amino-3-(1-methyltetrazol-5-ylthiomethyl)-Δ³-cephem-4-carboxylic acid.

What is claimed is:

1. A process of producing a 7-amino-3-heterocyclic thiomethyl-Δ³-cephem-4-carboxylic acid represented by the formula

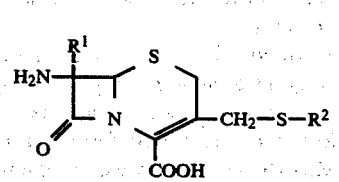

wherein R¹ represents a hydrogen atom or a methoxy group and R² represents a member selected from the group consisting of a thiazolyl group, an oxazolyl group, an isothiazolyl group, a thiadiazolyl group, a triazolyl group, and a tetrazolyl group, which are substitutable by a lower alkyl group, a carboxy lower alkyl group, a di-lower alkylamino lower alkyl group wherein lower alkyl represents 1 to 6 carbon atoms, and an amino group, or the pharmaceutically acceptable salts thereof, which comprises reacting a 7-amino cephalosporanic acid represented by the formula

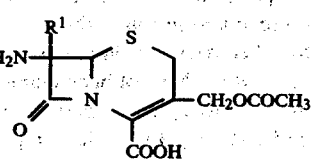

wherein R¹ is defined above and the alkali metal, ammonium or organic base salts thereof and a thiol represented by the general formula

HS—R² wherein $R^2$ is defined above, in a substantially anhydrous medium consisting essentially of concentrated or fuming sulfuric acid.

2. A process according to claim 1 wherein said 7-aminocephalosporanic acid is reacted with at least an equimolar amount of said thiol and the reaction is conducted at a temperature not in excess of room temperature.

3. A process according to claim 1 wherein said 7-aminocephalosporanic acid is reacted with at least an equimolar amount of said thiol and the reaction is conducted under heating.

4. A process according to claim 1 wherein the amount of sulfuric acid used is in excess of 2 mole times the amount of said 7-aminocephalosporanic acid.

5. A process according to claim 1 wherein the amount of sulfuric acid used is in excess of 5 mole times the amount of said 7-aminocephalosporanic acid.

6. A process according to claim 1 wherein 7-amino-3-(1-methyltetrazol-5-ylmethyl)-$\Delta^3$-cephem-4-carboxylic is obtained by reacting 5-mercapto-1-methyltetrazol and 7-aminocephalosporanic acid.

7. The process of claim 1 wherein said medium further contains polyphosphoric acid.

8. The process of claim 1 further comprising dispersing the reaction mixture in ice water at a pH sufficient to deposit said 7-amino-3-heterocyclic thiomethyl-$\Delta^3$-cephem-4-carboxylic acid.

* * * * *